US012758420B2

(12) United States Patent
Sekido et al.

(10) Patent No.: US 12,758,420 B2
(45) Date of Patent: Oct. 13, 2026

(54) EAR-FITTING DEVICE AND WARMING DEVICE

(71) Applicant: KOBAYASHI PHARMACEUTICAL CO., LTD., Osaka (JP)

(72) Inventors: Yuji Sekido, Ibaraki (JP); Ryota Asano, Ibaraki (JP); Yoshihiro Ujihara, Ibaraki (JP)

(73) Assignee: KOBAYASHI PHARMACEUTICAL CO., LTD., Osaka (JP)

( * ) Notice: Subject to any disclaimer, the term of this patent is extended or adjusted under 35 U.S.C. 154(b) by 512 days.

(21) Appl. No.: 18/251,398

(22) PCT Filed: Oct. 18, 2021

(86) PCT No.: PCT/JP2021/038397
§ 371 (c)(1),
(2) Date: May 2, 2023

(87) PCT Pub. No.: WO2022/097461
PCT Pub. Date: May 12, 2022

(65) Prior Publication Data

US 2023/0404797 A1 Dec. 21, 2023

(30) Foreign Application Priority Data

Nov. 6, 2020 (JP) ................................ 2020-186130

(51) Int. Cl.

| | |
|---|---|
| ***A61F 7/03*** | (2006.01) |
| *A61F 7/00* | (2006.01) |
| *A61F 7/02* | (2006.01) |

(52) U.S. Cl.
CPC ........ *A61F 7/03* (2013.01); *A61F 2007/0005* (2013.01); *A61F 2007/0225* (2013.01)

(58) Field of Classification Search
CPC ...... A61F 2007/0005; A61F 2007/0225; A61F 2007/0242; A61F 7/03; A61F 7/032; A61F 7/034
See application file for complete search history.

(56) References Cited

U.S. PATENT DOCUMENTS 3,796,855 A 3/1974 Brown et al.

FOREIGN PATENT DOCUMENTS

| | | | |
|---|---|---|---|
| CA | 2839225 | A1 | 7/2015 |
| CN | 208492677 | U | 2/2019 |

(Continued)

OTHER PUBLICATIONS

Dec. 3, 2024, Office Action issued by the UK Intellectual Property Office in the corresponding UK Patent Application No. 2306652.5.

(Continued)

*Primary Examiner* — Tigist S Demie
(74) *Attorney, Agent, or Firm* — KENJA IP LAW PC

(57) ABSTRACT

Disclosed is an ear-fitting device and a warming device configured to suppress burn of an ear by a warming body. The ear-fitting device according to the disclosure is wearable on an ear and includes a contact portion for contacting a predetermined site of an auricle, and a retainer portion for retaining a warming body capable of warming the predetermined site of the auricle through the contact portion. The retainer portion serves to retain the warming body via the contact portion, in a state where it is spaced from the contact portion.

4 Claims, 10 Drawing Sheets

(56) References Cited

FOREIGN PATENT DOCUMENTS

| | | | | |
|---|---|---|---|---|
| JP | 3082758 | U | | 12/2001 |
| JP | 2006320363 | A | * | 11/2006 |
| JP | 2014068831 | A | | 4/2014 |
| JP | 2018086202 | A | | 6/2018 |
| WO | 2012150363 | A1 | | 11/2012 |

OTHER PUBLICATIONS

Jul. 29, 2024, Office Action issued by the UK Intellectual Property Office in the corresponding UK Patent Application No. 2306652.5.
May 28, 2024, Office Action issued by the IP Australia in the corresponding Australian Patent Application No. 2021374137.
Dec. 28, 2021, International Search Report issued in the International Patent Application No. PCT/JP2021/038397.
Nov. 6, 2025, Office Action issued by the China National Intellectual Property Administration in the corresponding Chinese Patent Application No. 202180003990.2.
May 26, 2026, Office Action issued by the China National Intellectual Property Administration in the corresponding Chinese Patent Application No. 202180003990.2.

* cited by examiner

EAR-FITTING DEVICE AND WARMING DEVICE

TECHNICAL FIELD

This disclosure relates to an ear-fitting device and a warming device.

BACKGROUND

Patent Literature 1 describes a warming device that is wearable on the ear. The warming device described in Patent Literature 1 is a bag or a bag-like object configured to the size of the ear, with an opening for inserting the ear. Furthermore, the warming device described in Patent Literature 1 has a wearing portion that covers the ear either partly or entirely and that has a heat-generating portion.

CITATION LIST

Patent Literature

PTL 1: JP 2018-086202 A

SUMMARY

Technical Problem

The warming device described in Patent Literature 1 still has a room for further improvement in terms of suppressing burns of the ear caused by the heat-generating portion as a warming body.

It is an object of the disclosure to provide an ear-fitting device and a warming device having a configuration that is capable of suppressing burns of the ear caused by a warming body.

Solution to Problem

According to a first aspect of the disclosure, there is provided an ear-fitting device configured to be worn on an ear, comprising: a contact portion for contacting a predetermined site of an auricle; and a retainer portion for retaining a warming body configured to heat the predetermined site of the auricle through the contact portion; the retainer portion being configured to retain the warming body in a state where it is spaced from the contact part with a gap therebetween.

In one embodiment of the disclosure, the retainer portion is configured to retain the warming body in a state where the warming body is covered with the contact portion.

In one embodiment of the disclosure, the contact portion comprises: an annular side wall configured to be fitted to an ear concha; and a top plate portion that continues to one end of the annular side wall and having a contact surface configured to contact the bottom surface of the ear concha; wherein the retainer portion is configured to retain the warming body in a state where the warming body is accommodated inside the annular side wall from the back side of the contact surface.

In one embodiment of the disclosure, the retainer portion is configured to retain a hold portion that projects from a body portion of the warming body, in a state where the body portion of the warming body is accommodated inside the annular side wall from the back side of the contact surface; and the body portion of the warming body is spaced from the top plate portion with a gap therebetween, in a state where the retainer portion holds the hold portion of the warming body and the hold portion of the warming body is in contact with the other end of the annular side wall.

In one embodiment of the disclosure, the body portion of the warming body is spaced from the annular sidewall with a gap therebetween, in a state where the retainer portion holds the hold portion of the warming body and the hold portion of the warming body is in contact with the other end of the annular side wall.

In one embodiment of the disclosure, the retainer portion is configured to retain the warming body such that a distance from the contact portion to the warming body across the gap is greater than 0 mm and equal to or less than 1 mm.

According to a second aspect of the disclosure, there is provided a warming device comprising the aforementioned ear-fitting device and the warming body.

Advantageous Effect

According to the disclosure, it is possible to provide an ear-fitting device and a warming device capable of suppressing ear burns by a warming body.

DETAILED DESCRIPTION

Figure 1:
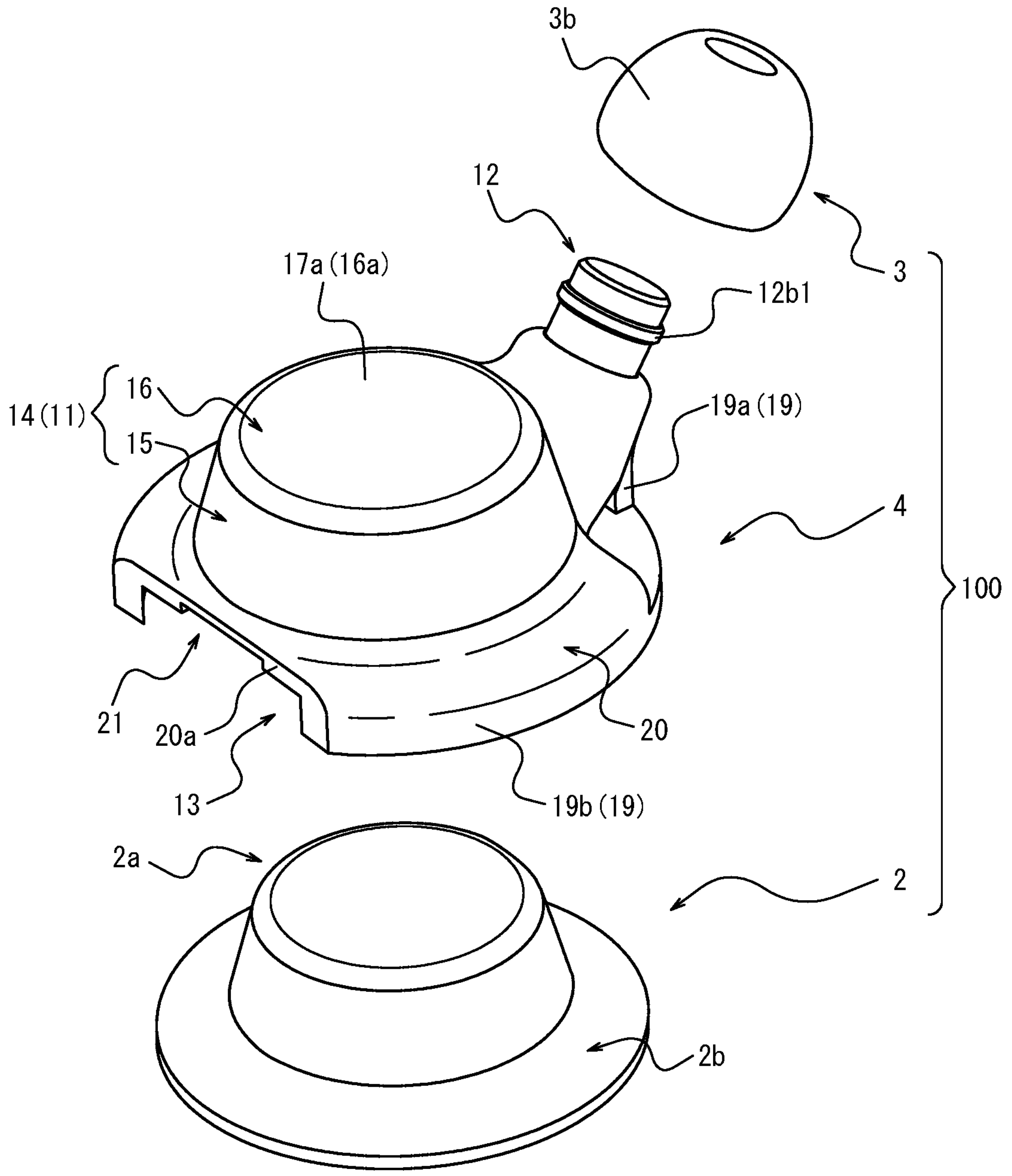
FIG. 1 is an exploded perspective view of a warming device according to an embodiment of the disclosure.

Hereinafter, embodiments of an ear-fitting device and a warming device according to the disclosure will be described below, by way of example, and with reference to the drawings. The same reference numerals are afforded to the configurations that are common in each figure.

Figure 2:
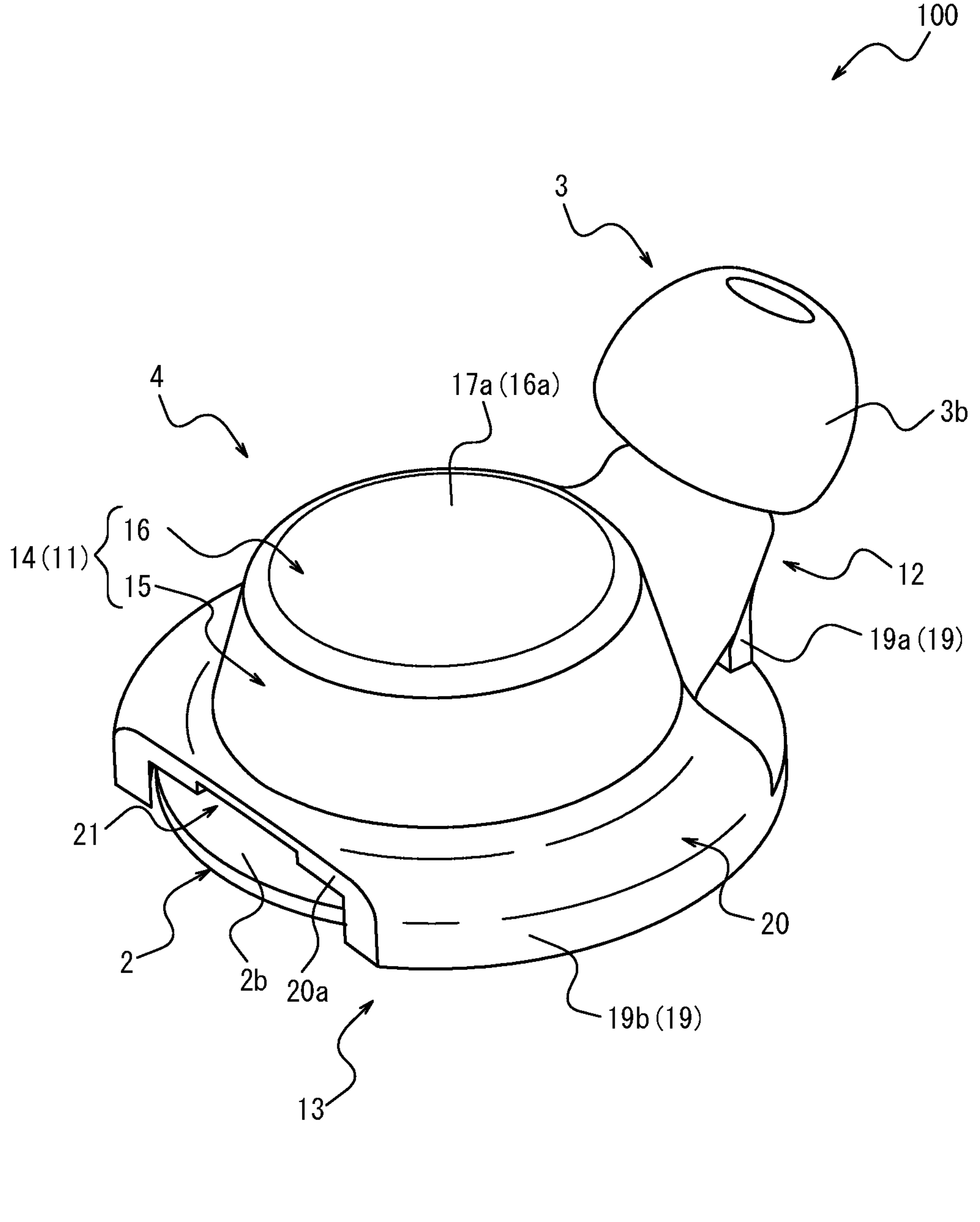
FIG. 2 is a perspective view depicting the warming device of FIG. 1 in use.

FIGS. 1 and 2 are perspective views depicting a warming device 100 as one embodiment of the warming device according to the disclosure. As depicted in FIGS. 1 and 2, the warming device 100 includes a warming body 2, a cover member 3, as well as an ear-fitting device 4 as one embodiment of the ear-fitting device according to the disclosure. FIG. 1 is an exploded perspective view of the warming device 100. FIG. 2 is a perspective view of the warming device 100 in use. The warming device 100 may be distributed on the market in a state where the warming body 2, the cover member 3 and the ear-fitting device 4 are separately disassembled (see FIG. 1), or it may be distributed on the market in a use state (see FIG. 2) with the warming body 2 and the cover member 3 attached to the ear-fitting device 4. Furthermore, the warming body 2, the cover member 3 and the ear-fitting device 4, which constitute the warming device 100, may be distributed separately on the market.

Figure 3:
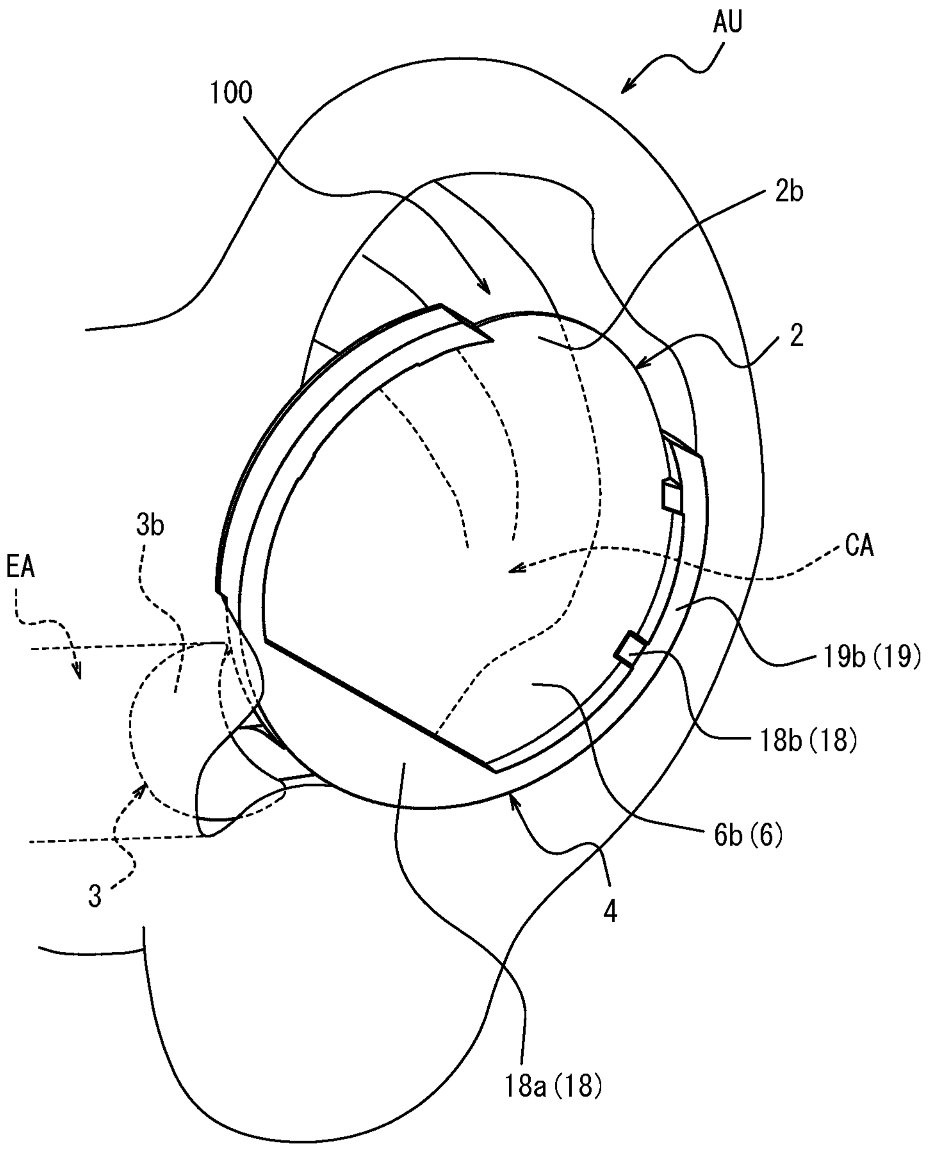
FIG. 3 is a diagram depicting a state where the warming device of FIG. 2 is in use as being worn on the ear.

FIG. 3 is a diagram depicting a state where warming device 100 depicted in FIG. 2 in a use state is worn on the user's ear. As depicted in FIG. 3, the warming device 100 according to the present embodiment is used by being worn on the ear. Although the details will be described hereinafter, according to the warming device 100, a predetermined site of the ear can be warmed by the warming body 2 while being worn on the user's ear. By warming the ears, poor blood circulation can be improved, thereby improving such symptoms as dizziness, tinnitus, headache, stiff shoulders, etc. (hereinafter referred to as "dizziness, etc."). Also, by warming the ear, the internal parasympathetic nerves are stimulated by the warming, and a relaxing effect can be obtained.

As depicted in FIG. 3, the warming device 100 of the present embodiment can be fixed to the ear by inserting the cover member 3 into the external auditory canal EA, which is the so-called ear canal, and fitting the ear-fitting device 4 into the ear concha CA of the auricle AU. Attachment of the warming device 100 of the present embodiment to the ear is completed by fixing it in this manner. However, the manner of fixing the warming device 100 is not particularly limited as long as it can be worn on the ear. The warming device 100 may be fixed to the ear, for example, only by inserting it into the external auditory canal EA and tightly fitting to the inner surface of the external auditory canal EA. Alternatively, the warming device 100 may be fixed to the ear only by inserting it into the ear concha CA and tightly fitting it to the inner surface of the ear concha CA. Furthermore, the warming device 100 may be fixed to the ear by pinching any part of the auricle AU other than the ear concha CA.

The details of each of the warming body 2, the cover member 3, and the ear-fitting device 4 of the warming device 100 will be described below.

<Warming Body 2>

Figure 4:
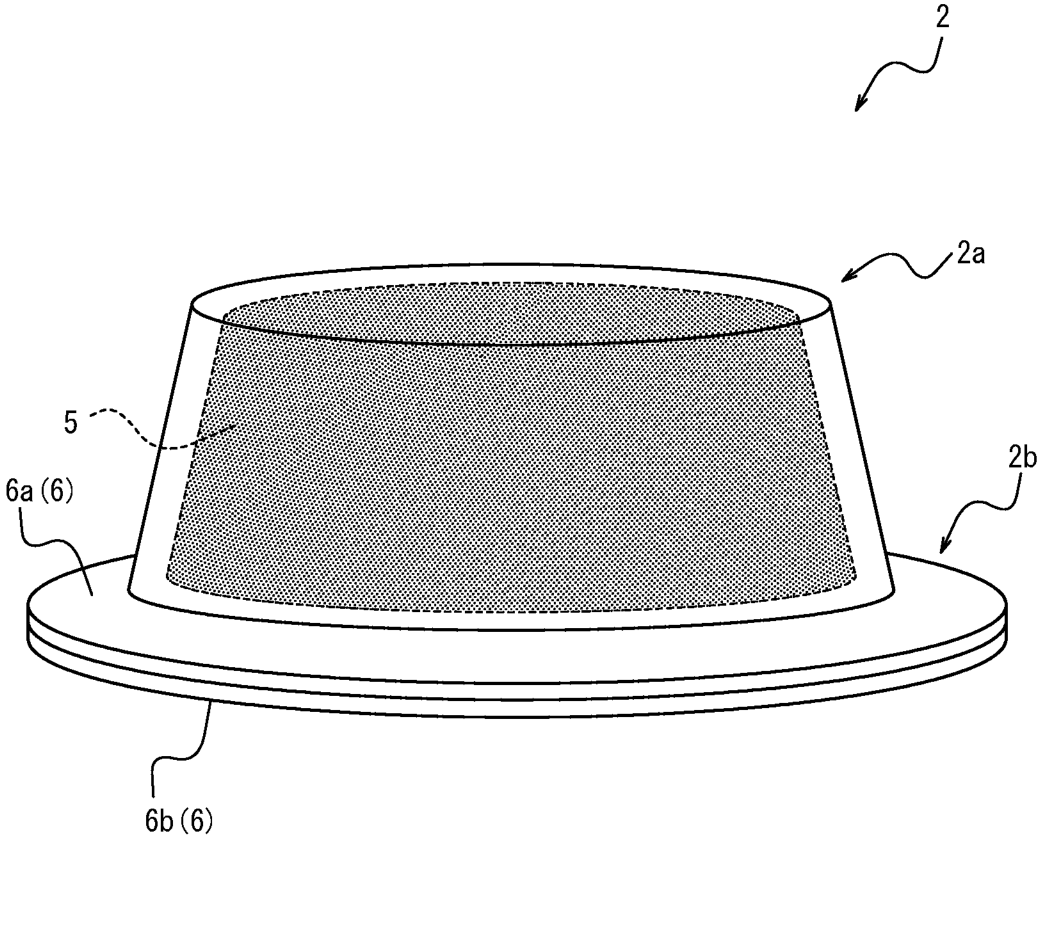
FIG. 4 is a diagram depicting a single warming body of the warming device of FIG. 1.

FIG. 4 is a diagram depicting the warming body 2. The warming body 2 in the present embodiment is a disposable body warmer. The warming body 2 before use is sealed in an airtight film bag. The warming body 2 before use may be sealed in a film bag as a single warming body 2. Alternatively, it may be sealed in a film bag together with the ear-fitting device 4, as being attached in advance to the ear-fitting device 4.

The warming body 2 according to the present embodiment includes an exothermic composition 5 that undergoes a chemical reaction for generating heat when exposed to air, and a container 6 for accommodating the exothermic composition 5 therein. The exothermic composition 5 includes, for example, appropriate amount of oxidizable metals (iron powder, etc.), activated carbon, carbon black, water retention agents (wood powder, vermiculite, diatomaceous earth, perlite, silica gel, alumina, water-absorbing resin, etc.), metal salts (salt, etc.), and water, etc. The container 6 of the present embodiment includes a first sheet **6*a* and a second sheet 6*b* that contain the exothermic composition 5 sandwiched therebetween. The first sheet 6*a* and the second sheet 6*b* are joined together at their peripheral edges, for example, by adhesion or welding, with the exothermic composition 5** sandwiched therebetween.

The heat-generating composition 5 is sandwiched between the first sheet **6*a* and the second sheet 6*b* so that the first sheet 6*a* has a hat shape and the second sheet 6*b* has a circular flat shape. Although the details will be described later, the warming body 2 according to the present embodiment is attached to the ear-fitting device 4 so that the first sheet 6*a* is covered with the ear-fitting device 4 (see FIG. 9). On the other hand, the warming body 2 according to the present embodiment is attached to the ear-fitting device 4 with the second sheet 6*b* being exposed to the outside (see FIGS. 3 and 9**).

In this embodiment, the air permeability of the first sheet **6*a* is higher than that of the second sheet 6*b*. By this, with the warming body 2 attached to the ear-fitting device 4, it is possible to suppress heat radiation through the second sheet 6*b* exposed to the outside. In particular, in the present embodiment, the first sheet 6*a* is preferably a moisture-permeable sheet, and the second sheet 6*b*** is preferably a moisture-impermeable sheet.

The first sheet **6*a* may be made, for example, of a highly air-permeable material or may be made of a material in which air holes are appropriately formed. Examples of materials for forming the first sheet 6*a* may include woven fabrics, non-woven fabrics, synthetic resins, rubbers, elastomers, and the like. The second sheet 6*b* may be made, for example, of a material with low air permeability. Examples of the material forming the second sheet 6*b*** may include synthetic resins, laminates of synthetic resins and woven fabrics or non-woven fabrics, and the like.

Examples of fiber materials forming the woven fabrics or non-woven fabrics with high air permeability may include synthetic fibers such as nylon, vinylon, polyester, rayon, acrylic, polyethylene, polypropylene, acetate, polyvinyl chloride, and polybutylene terephthalate, natural fibers such as cotton, hemp, silk and paper, as well as mixed fibers of synthetic and natural fibers. These fiber materials may be used either alone or in combination of two or more.

As the material constituting the synthetic resin having low air permeability, for example, resin materials similar to the fiber material described above may be used. Thus, the second sheet **6*b* may be, for example, a resin film made of the resin material exemplified with respect to the fiber material described above. Also, the first sheet 6*a* may be made of a resin film similar to the second sheet 6*b***, in which ventilation holes are appropriately formed.

As described above, the warming body 2 in the present embodiment includes the exothermic composition 5 that causes a chemical reaction for generating heat when exposed to air, though it is not limited to this configuration. The warming body 2 may be configured to store heat for a predetermined period of time and may be used after being heated in a microwave oven, for example. Furthermore, the warming body 2 may be, for example, one that utilizes the heat of solidification of a sodium acetate aqueous solution that is in a supercooled state at room temperature.

Moreover, in the warming body 2 of the present embodiment, the container 6 enclosing the exothermic composition 5 is composed of the first sheet **6*a* and the second sheet 6*b*, though it is not limited to this configuration. The configuration of the container 6 is not particularly limited as long as it is configured to accommodate and hold the exothermic composition 5 so as to correspond to the configuration of the ear attachment 4**.

The portion of the warming body 2 in the present embodiment, which accommodates the exothermic composition 5, is hereinafter referred to as a body portion **2*a* of the warming body 2. The body portion 2*a* in the present embodiment has a substantially frusto-conical outer shape, though the outer shape is not particularly limited. Furthermore, hereinafter, the portion of the warming body 2 in the present embodiment, which projects from the main body portion 2***a*, will be referred to as a hold portion 2*b*. The hold portion 2*b* in the present embodiment comprises a flange portion that projects radially outward from the large-diameter side end portion of the truncated cone-shaped body portion 2*a*. Furthermore, the hold portion 2*b* in the present embodiment is configured by peripheral edge portions of the first sheet 6*a* and the second sheet 6*b*.

<Cover Member 3>

As depicted in FIGS. 1 and 2, the cover member 3 is configured to be attachable to an insert portion 12 of the ear-fitting device 4, which will be described hereinafter. More specifically, the cover member 3 in the present embodiment includes a mounting tube portion 3*a* (see FIG. 9) for fitting the insert portion 12 of the ear-fitting device 4 therein, and an outer tube portion 3*b* that is continuous with, and folded back from the tip of the mounting tube portion 3*a*.

The insert portion 12 of the ear-fitting device 4 is configured such that it can be inserted into the mounting tube portion 3*a* of the cover member 3 through an opening on the base end side. The insert portion 12 is configured to retain the mounting tube portion 3*a* by being brought into close contact with the inner surface of the mounting tube portion 3*a*. Although details will be described hereinafter, the insert portion 12 of the ear-fitting device 4 according to the present embodiment includes an annular convex portion 12*b*1. The annular convex portion 12*b*1 of the insert portion 12 is configured to fit into an annular concave portion 3*a*1 (see FIG. 9) provided in the inner surface of the mounting tube portion 3*a*. This makes it possible to enhance the retention of the cover member 3 by the insert portion 12.

The outer tube portion 3*b* is configured to cover the radially outer side of the mounting tube portion 3*a*. An annular space is defined between the mounting tube portion 3*a* and the outer tube portion 3*b*. Thus, when the outer tube portion 3*b* is inserted into the external auditory canal EA as depicted in FIG. 3, it is brought into close contact with the inner surface of the external auditory canal EA while being elastically deformed. In this manner, by attaching the cover member 3 to the ear-fitting device 4, the cover member 3 is fitted into the external auditory canal EA to be in close contact with the inner surface of the external auditory canal EA, thereby enhancing the fixing property of the warming device 100 by the external auditory canal EA. Moreover, by using the cover member 3, it is possible to close the external auditory canal EA improve the sound insulation property. This makes it possible to block external noise, etc., thereby realizing a state where the user wearing the warming device 100 can be relaxed easily.

Although the material constituting the cover member 3 is not particularly limited, examples thereof include rubber, elastomer, synthetic resin including soft resin and hard resin, and the like. Examples of synthetic resins that can be used include polypropylene (PP), polyethylene (PE), polyethylene terephthalate (PET), and the like. In the cover member 3 of the present embodiment, the mounting tube portion 3*a* and the outer tube portion 3*b* are integrally formed of the same material, but they may be formed of separate materials. Further, the cover member 3 may have a structure in which a material such as metal or carbon is mixed with a base material such as rubber, elastomer, or synthetic resin. Furthermore, the cover member 3 may be made of a thermally conductive resin.

<Ear-Fitting Device 4>

The ear-fitting device 4 is configured so that the warming body 2 and the cover member 3 described above can be attached. The ear-fitting device 4 is further configured so as to be worn on the ear together with the attached warming body 2 and cover member 3. Note that the phrase "the ear-fitting device 4 can be worn on the ear" means not only the case where the ear-fitting device 4 itself can be fixed to the ear directly, but also the case where the ear-fitting device 4 can be fixed to the ear indirectly, for example, through another member, such as the cover member 3.

Figure 5A:
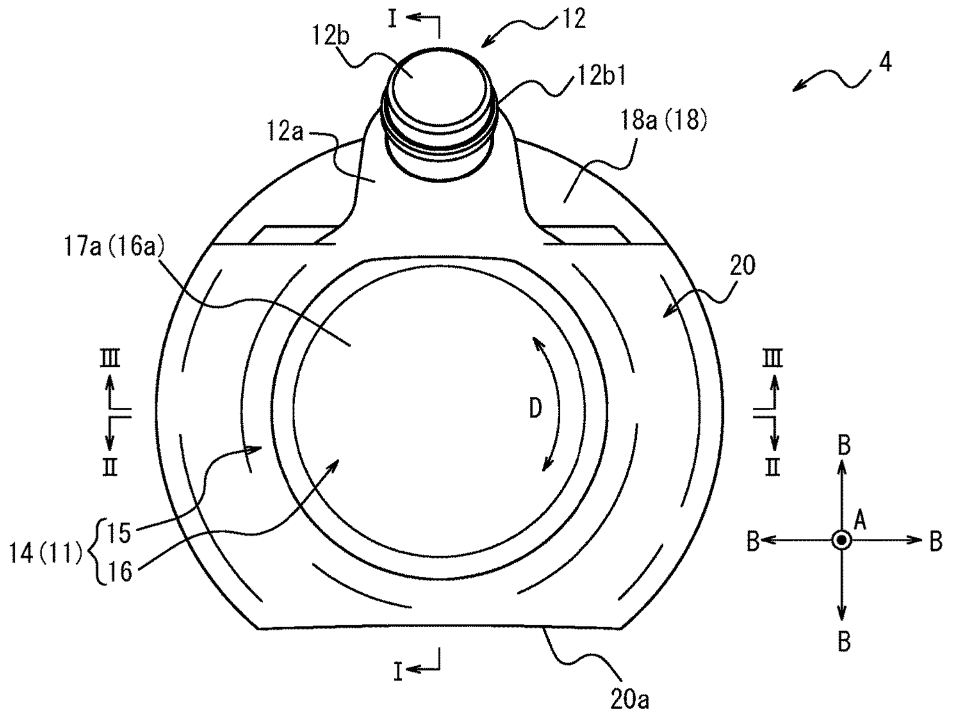
FIGS. 5A and 5B are a top view and a bottom view of a single ear-fitting device of the warming device of FIG. 1, respectively.
Figure 5B:
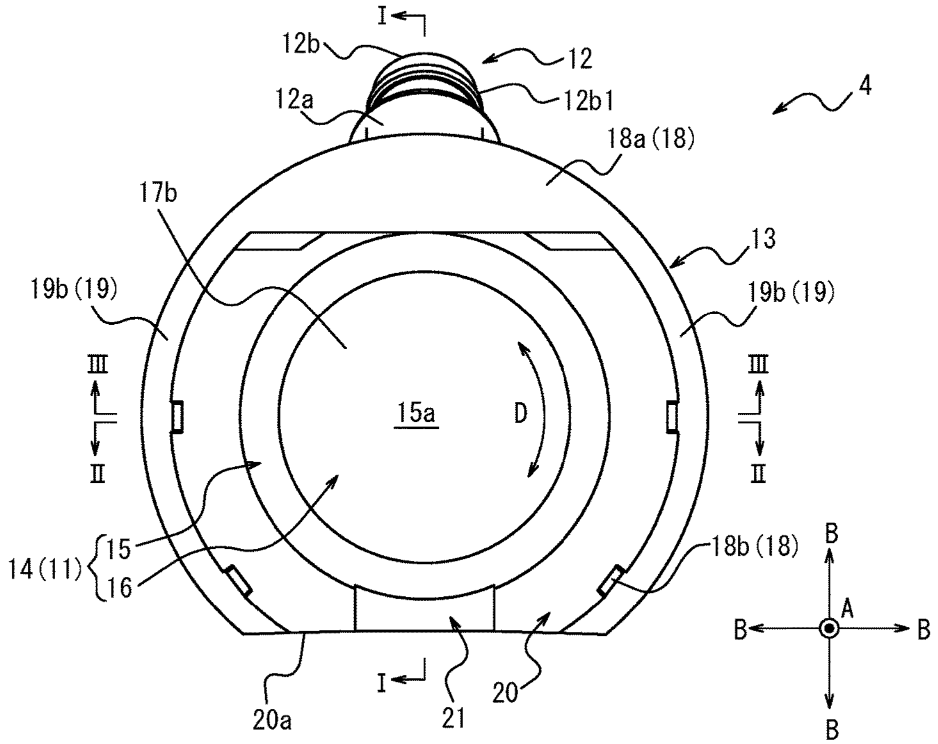
Figure 6:
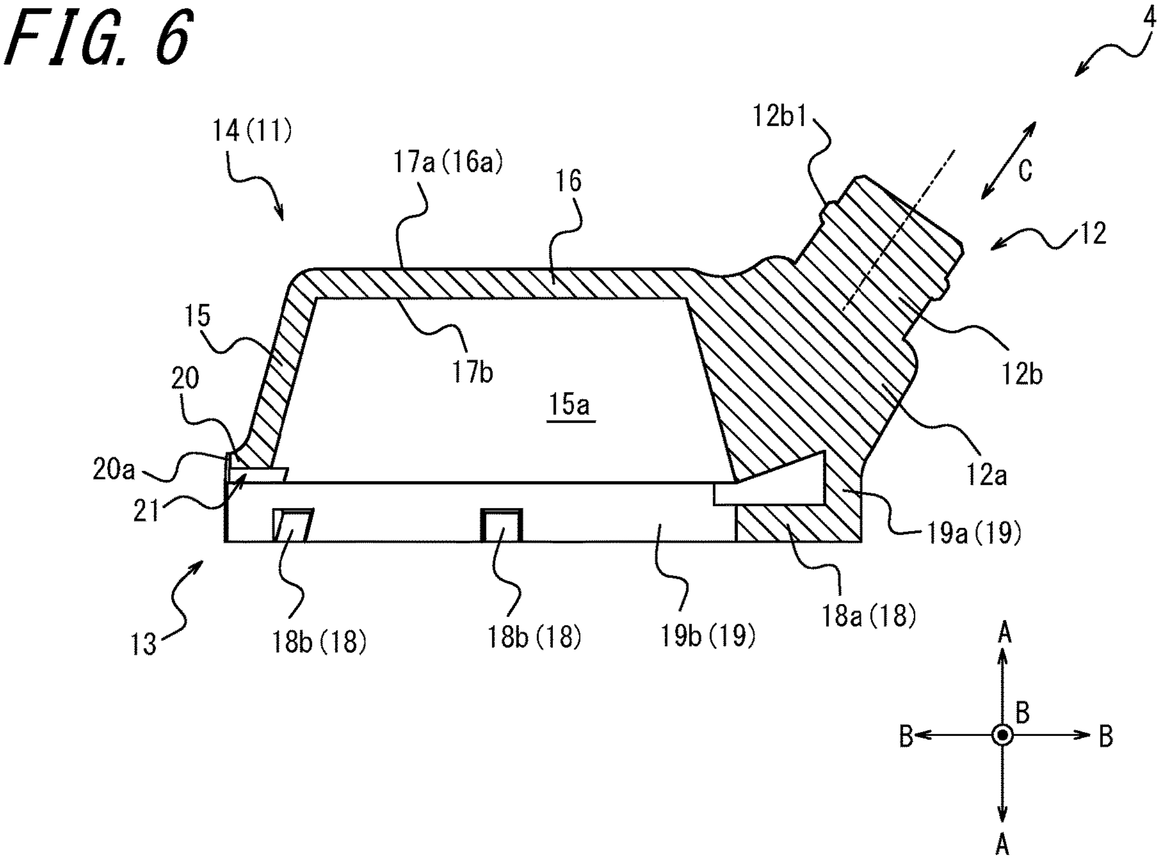
FIG. 6 is a sectional view along the line I-I in FIGS. 5A and 5B.
Figure 7:
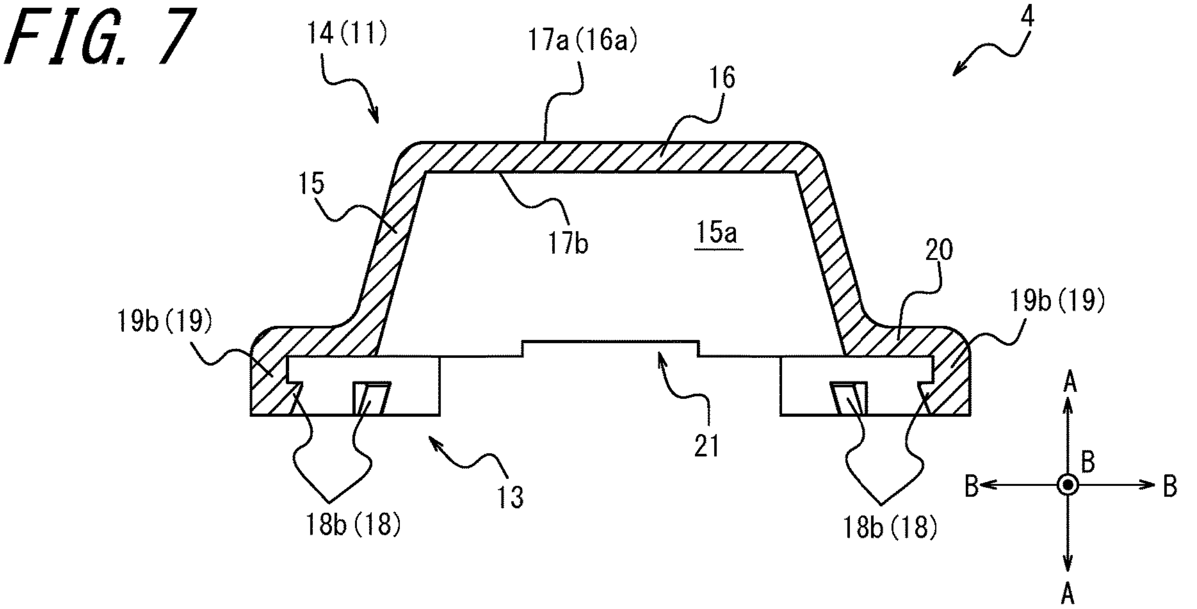
FIG. 7 is a sectional view along the line II-II in FIGS. 5A and 5B.
Figure 8:
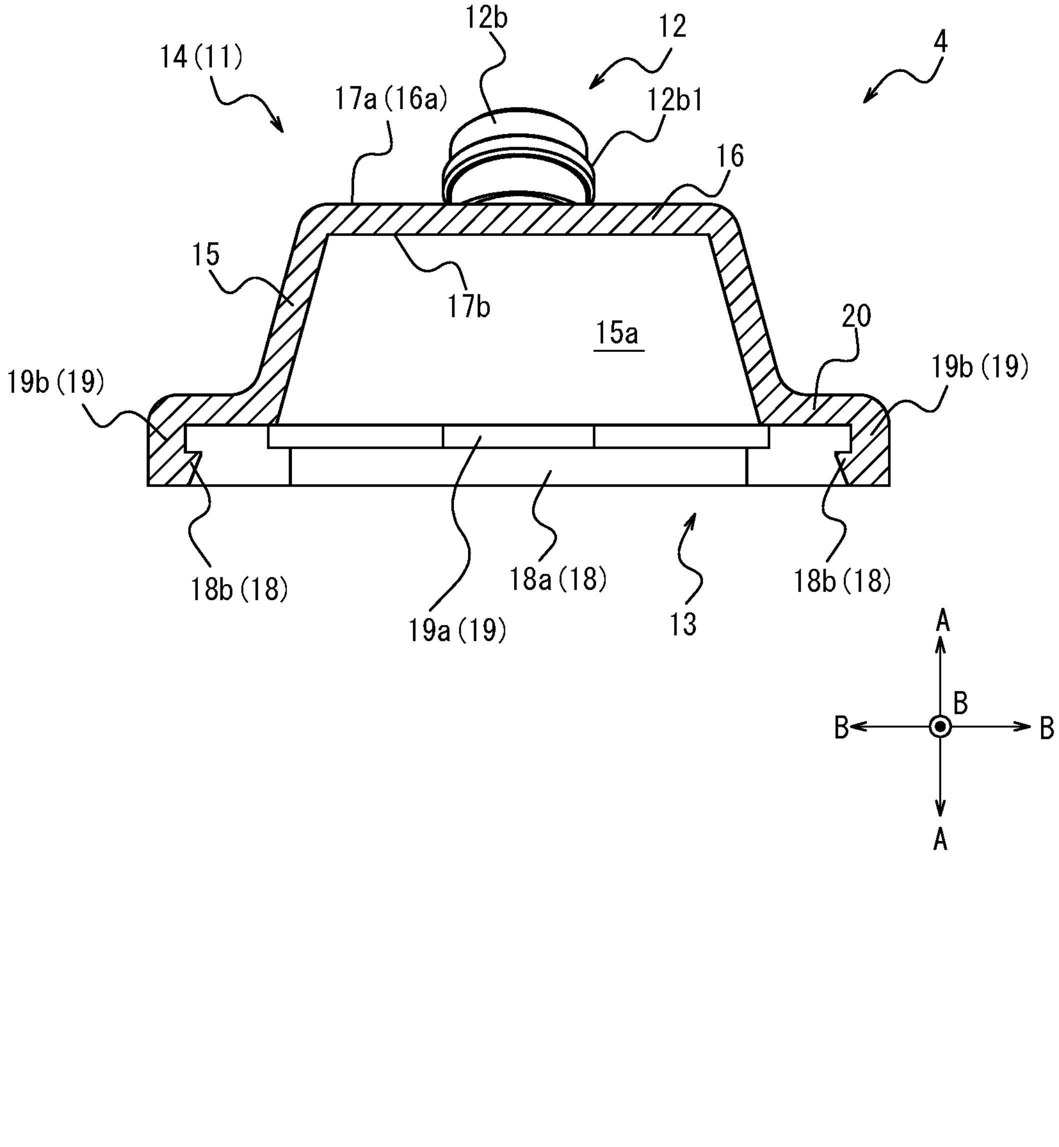
FIG. 8 is a sectional view along the line in FIGS. 5A and 5B.

FIG. 5A is a top view of the ear-fitting device 4 alone, as seen from the upper surface side. FIG. 5B is a bottom view of the ear-fitting device 4 alone, as seen from the lower surface side. Here, the term "upper surface" of the ear-fitting device 4 means the surface positioned on the auricle AU (see FIG. 3) side when the ear-fitting device 4 is worn on the ear. Also, the term "lower surface" of the ear-fitting device 4 means the surface opposite to the upper surface. FIG. 6 is a cross-sectional view of the ear-fitting device 4 taken along line I-I in FIGS. 5A and 5B. FIG. 7 is a cross-sectional view of the ear-fitting device 4 taken along line II-II in FIGS. 5A and 5B. FIG. 8 is a cross-sectional view of the ear-fitting device 4 taken along line III-III in FIGS. 5A and 5B. The details of the ear-fitting device 4 will be described below with reference to FIGS. 1 to 3 and 5 to 8.

As depicted in FIG. 1 and the like, the ear-fitting device 4 according to the present embodiment includes a contact portion 11, an insert portion 12, a retainer portion 13, and a connecting collar 20.

<Contact Portion 11>

The contact portion 11 is configured to contact a predetermined site of the auricle AU when the ear-fitting device 4 is worn on the ear (see FIG. 3). In the state where the ear-fitting device 4 is attached to the ear (see FIG. 3), the predetermined site of the auricle AU with which the contact portion 11 contacts is not particularly limited. By warming an arbitrary portion of the auricle AU with the warming body 2 through the contact portion 11, it is possible to improve poor blood circulation, and expect improvement of symptoms such as dizziness. Further, internal parasympathetic nerves are stimulated by warming, and a relaxing effect can be obtained.

As depicted in FIG. 3, the contact portion 11 in the present embodiment is configured by a fitting portion 14 that can be fitted into the ear concha CA of the auricle AU. The fitting portion 14 is configured to be fitted into the ear concha CA so as to come into contact with the inner surface of the ear concha CA as the predetermined site of the auricle AU. More specifically, the fitting portion 14 as the contact portion 11 of the present embodiment is fitted into the ear concha CA so as to come into contact with the inner surface of the concha cavum among the inner surfaces of the ear concha CA. As described above, the predetermined site of the auricle AU with which the contact portion 11 contacts is not particularly limited. However, preferably, the fitting portion 14 is configured to be brought into contact with the inner surface, and particularly preferably the fitting portion 14 is configured to be brought into contact with the inner surface of the concha cavum. By warming the inner surface of the ear concha CA with the warming body 2 through the fitting portion 14 as the contact portion 11, the internal parasympathetic nerves can be efficiently warmed. As a result, the relaxing effect described above can be further enhanced.

Hereinafter, for convenience of explanation, the extending direction of the fitting portion 14 is referred to as "the height direction A of the fitting portion 14" or simply as "the height direction A". The fitting portion 14 in the present embodiment has a substantially frusto-conical outer shape. Thus, the height direction A of the fitting portion 14 in the present embodiment is the central axis direction of the annular side wall 15 (see FIG. 1 etc.), which will be described later. Further, hereinafter, for convenience of explanation, the direction from the base end side to the tip end side of the fitting portion 14 in the height direction A of the fitting portion 14 may be simply referred to as the "upper side". Further, in the height direction A of the fitting portion 14, the direction from the tip end side to the base end side of the fitting portion 14 may be simply referred to as the "lower side". The upper side in the present embodiment means one end side of the annular side wall 15 (see FIG. 1 etc.) where the top plate portion 16 (see FIG. 1 etc.) continues. The lower side in the present embodiment means the other end side opposite to the one end side, where the top plate portion 16 continues in the annular side wall 15.

As depicted in FIGS. 5A to 8, the fitting portion 14 as the contact portion 11 in the present embodiment defines an accommodation space 15*a* inside, configured to accommodate the warming body 2 for heating the inner surface of the ear concha CA through the fitting portion 14. The fitting portion 14 in the present embodiment includes a convex surface configured to contact the inner surface of the ear concha CA, and a concave surface defining the accommodation space 15*a* behind the convex surface. Specifically, the fitting portion 14 as the contact portion 11 in the present embodiment includes an annular side wall 15 and a top plate portion 16. The annular side wall 15 is configured to be fitted with the ear concha CA. In particular, the annular side wall 15 in the present embodiment is configured to be fitted so as to be sandwiched by the inner side surfaces of the concha CA. More specifically, among the inner side surfaces of the ear concha CA, the annular side wall 15 in the present embodiment is configured to be fitted so as to be sandwiched by the inner side surfaces of the concha cavum. The annular side wall 15 defines an accommodation space 15*a* where the body portion 2*a* (see FIG. 4) of the warming body 2 can be accommodated. The top plate portion 16 is connected to an upper side end (hereinafter referred to as the "upper end") of the annular side wall 15. The upper end of the accommodation space 15*a* of the annular side wall 15 is closed by the top plate portion 16. In other words, the accommodation space 15*a* in the present embodiment is a frusto-conical space that is defined by the annular side wall 15 and the top plate portion 16. The top plate portion 16 has a contact surface 16*a* configured to contact the bottom surface of the ear concha CA in a state where the annular side wall 15 is fitted to the ear concha CA. More specifically, among the bottom surfaces of the ear concha CA, the contact surface 16*a* in the present embodiment is configured to contact the bottom surface of the concha cavum. The contact surface 16*a* of the top plate portion 16 in the present embodiment is constituted by the top plate upper surface 17*a* on the opposite side of the top plate lower surface 17*b* facing the accommodation space 15*a* of the top plate portion 16.

The above-described warming body 2 is attached to the ear fitting device 4 by accommodating the body portion 2*a* in the accommodation space 15*a*. Specifically, the body portion 2*a* of the warming body 2 can be accommodated in the accommodation space 15*a* from an open end, which is a lower side end (hereinafter referred to as "the lower end") opposite to the upper end that is connected to the top plate portion 16 of the annular side wall 15. The body portion 2*a* of the warming body 2 is accommodated in the accommodation space 15*a* without contacting the annular side wall 15 and the top plate portion 16, rather, as being spaced from the annular side wall 15 and the top plate portion 16 with a gap X (see FIG. 9). The details of this arrangement will be described hereinafter (with reference to FIG. 9).

The fitting portion 14 in the present embodiment has an outer shape that is a frusto-conical shape, though there is no particular limitations on the outer shape. The outer shape of the fitting portion 14 may be cylindrical, for example. Further, the outer shape of the fitting portion 14 may be, for example, a shape corresponding to the inner surface of the ear concha CA. Thus, the annular side wall 15 of the fitting portion 14 is not limited to the tapered tubular shape of the present embodiment. The annular side wall 15 may have a cylindrical shape having uniform inner and outer diameters regardless of the position in the central axis direction. However, as in the present embodiment, it is preferred that the outer surface of the annular side wall 15 has a tapered shape tapering from the lower end opposite to the upper end where the top plate portion 16 continues toward the upper end. By this, it becomes easier to fit the fitting portion 14 into the ear concha CA. Further, it is not always necessary for the annular side wall 15 to have a circular cross-sectional shape perpendicular to the height direction A; the cross-sectional shape may be an endless shape corresponding to the inner surface of the ear concha CA. Moreover, the top plate portion 16 in the present embodiment is constituted by a circular flat plate portion that closes the upper end of the tapered cylindrical annular side wall 15, though it is not limited to this arrangement. The top plate portion 16 is preferably configured so that the contact surface 16*a* can increase the area of contact with the bottom surface of the ear concha CA. Thus, the top plate portion 16 may be constituted, for example, by a curved plate portion that is curved in a dome shape so that the contact surface 16*a* is convex. Furthermore, although the accommodation space 15*a* in the present embodiment is a substantially truncated cone-shaped space, the shape of the accommodation space 15*a* is not particularly limited. It is sufficient for the accommodation space 15*a* in the present embodiment to be configured to accommodate at least a portion of the warming body 2, and may be configured to warm the auricle AU through the fitting portion 14. In the present embodiment, the main body portion 2*a* of the warming body 2 is accommodated in the accommodation space 15*a* so that the body portion 2*a* is covered with the annular side wall 15 and the top plate portion 16. The details of this arrangement will be described hereinafter (with reference to FIG. 9).

<Insert Portion 12>

As depicted in FIGS. 5A, 5B and 6, the insert portion 12 projects from the fitting portion 14 as the contact portion 11. The insert portion 12 is configured to be inserted into the external auditory canal EA (see FIG. 3) together with the attached cover member 3. Specifically, the insert portion 12 in the present embodiment projects outward from the fitting portion 14 in a plan view (see FIG. 5A) along the height direction A of the fitting portion 14. More specifically, the insert portion 12 in the present embodiment projects from the annular side wall 15 of the fitting portion 14 to the outside in the radial direction B of the annular side wall 15. Hereinafter, for convenience of explanation, the radial direction B of the annular side wall 15 may be simply referred to as "the radial direction B".

The insert portion 12 in the present embodiment includes a base end portion 12*a* connected to the annular side wall 15 and a tip end portion 12*b* connected to the base end portion 12*a* and configured to be inserted into the mounting tube portion 3*a* (see FIG. 9) of the cover member 3. The tip end portion 12*b* has a substantially cylindrical outer shape. A central axis direction C, which is an extending direction of the tip end portion 12*b*, is inclined with respect to the height direction A of the fitting portion 14. The tip end portion 12*b* is configured to be inserted into the mounting tube portion 3*a* of the cover member 3 so as to expand the mounting tube portion 3*a* radially outward. By this, the outer surface of the tip end portion 12*b* can be brought into close contact with the inner surface of the mounting tube portion 3*a*. As a result, the cover member 3 is held by the insert portion 12 of the ear-fitting device 4. In addition to the close contact between the outer tube portion 3*b* and the inner surface of the external auditory canal EA, the close contact of the outer surface of the tip end portion 12*b* with the inner surface of the mounting tube portion 3*a* allows the external auditory canal EA to be further closed, to further enhance the sound insulation of the warming tool 100.

Further, the tip end portion 12*b* in the present embodiment includes an annular convex portion 12*b*1 that projects radially outward. When the tip end portion 12*b* of the insert portion 12 is inserted into the mounting tube portion 3*a* of the cover member 3, the annular convex portion 12*b*1 of the tip end portion 12*b* engages with an annular concave portion 3*a*1 (see FIG. 9) provided on the inner surface of the mounting tube portion 3*a*. This makes it difficult for the attachment tube portion 3*a* to come off from the tip end portion 12*b*. It is thus possible to enhance the retention of the cover member 3 by the insert portion 12.

The insert portion 12 in the present embodiment is formed separately from the cover member 3 so that the cover member 3 can be attached thereto, though they may be formed integrally. Thus, the tip end portion 12*b* of the insert portion 12 in the present embodiment may be formed so as to be integrally connected to the mounting tube portion 3*a* of the cover member 3, for example.

Moreover, the ear-fitting device 4 in the present embodiment includes the insert portion 12, it is not limited to this arrangement. Although the ear-fitting device 4 in the present embodiment is configured to include the insert portion 12 configured to be fixed to the ear by being in close contact with the inner surface of the external auditory canal EA, if the ear-fitting device 4 is fixed only to the auricle AU, for example, it is not necessary for the ear-fitting device 4 to include the insert portion 12. However, from the viewpoint of the relaxation effect due to the sound insulation, it is preferred for the warming device 100 to include an insert portion 12 that can be inserted into the external auditory canal EA. Moreover, it is preferred that the warming device 100 further includes a cover member 3 attached to the insert portion 12 in order to enhance the adhesion to the inner surface of the external auditory canal EA. By this, it is possible to further enhance the relaxation effect due to the sound insulation. In addition, although the insert portion 12 of the present embodiment is formed integrally with the fitting portion 14, it may be formed separately from the fitting portion 14 and attached to the fitting portion 14 in a detachable manner.

<Retainer Portion 13>

The retainer portion 13 is configured to retain the warming body 2 for warming a predetermined site of the auricle AU through the contact portion 11. In other words, the warming body 2 held by the retainer portion 13 in the present embodiment is configured to warm the inner surface of the ear concha CA as a predetermined site of the auricle AU through the fitting portion 14 as the contact portion 11.

Further, although the details will be described hereinafter, the retainer portion 13 is configured to retain the warming body 2 while being spaced from the fitting portion 14 as the contact portion 11 with the gap X therebetween (see FIG. 9). By this, it is possible to suppress an abrupt temperature rise of the contact portion 11 due to the warming body 2 compared to a configuration where the contact portion 11 and the warming body 2 are in contact with each other without the gap X. It is thus possible to suppress burns of the predetermined site of the auricle AU (the inner surface of the ear concha CA in this embodiment) that contacts the contact portion 11.

As depicted in FIG. 5B, the retainer portion 13 in the present embodiment includes a support portion 18 for supporting the warming body 2 from below, as well as a restriction wall 19 for restricting a movement of the warming body 2 in a direction perpendicular to the height direction A.

More specifically, as depicted in FIGS. 6 to 8, the support portion 18 of the present embodiment includes a support plate portion 18*a* of a flat plate shape extending below the lower end of the fitting portion 14 in a direction perpendicular to the height direction A, and a support projection portion 18*b* projecting inward from the restriction wall 19 in the radial direction B. The hold portion 2*b* of the warming body 2 is supported from below by the support plate portion 18*a* and the support projection portion 18*b* with the body portion 2*a* accommodated in the accommodation space 15*a*. Thus, the support plate portion 18*a* and the support projection portion 18*b* are provided at positions that do not overlap the accommodation space 15*a* in the height direction A. More specifically, the support plate portion 18*a* and the support projection portion 18*b* of the support portion 18 in the present embodiment are provided at positions outside the accommodation space 15*a* in the radial direction B.

Further, the restriction wall 19 continues to the outer side of the support portion 18 in the radial direction B and extends upward in the height direction A. More specifically, as depicted in FIGS. 6 to 8, the restriction wall 19 in the present embodiment includes a first restriction wall portion 19*a* that continues to the outer side of the support plate portion 18*a* in the radial direction B and extends upward in the height direction A, and a second restriction wall portion 19*b* that continues to the outer side of the support projection portion 18*b* in the radial direction B and extends upward in the height direction A. The first and second restriction wall portions 19*a* and 19*b* are positioned outside the hold portion 2*b* in the radial direction B, with the hold portion 2*b* of the warming body 2 supported from below by the support plate portion 18*a* and the support projection portion 18*b*. Thus, in a state where the body portion 2*a* is accommodated in the accommodation space 15*a* and the hold portion 2*b* is supported from below by the support plate portion 18*a* and the support projection portion 18*b*, the hold portion 2*b* of the warming body 2 is restricted from moving in the direction perpendicular to the height direction A, by the first restriction wall portion 19*a* and the second restriction wall portion 19*b*.

As described above, the retainer portion 13 in the present embodiment serves to retain the warming body 2 by restricting the movement on the lower side in the height direction A and the movement in the direction perpendicular to the height direction A of the hold portion 2*b* of the warming body 2, by means of the support portion 18 and the restriction wall 19. The movement of the hold portion 2*b* of the warming body 2 on the upper side in the height direction A is restricted by the lower end of the fitting portion 14 described above. In particular, in the ear-fitting device 4 of the present embodiment, there is provided a connecting collar 20 that projects outward in the radial direction B from the lower end of the fitting portion 14, for connecting the fitting portion 14 and the second restriction wall portion 19*b* of the retainer portion 13 with each other. In the present embodiment, the connecting collar 20 serves to restrict the upward movement of the hold portion 2*b* of the warming body 2 in the height direction A, together with the lower end of the fitting portion 14. However, it is sufficient for the ear-fitting device 4 only to have a portion connecting the fitting portion 14 and the retainer portion 13, and its configuration is not limited to the connecting collar 20 as in the present embodiment. Thus, the upward movement of the hold portion 2*b* of the warming body 2 in the height direction A may be restricted only by the lower end of the fitting portion 14, and the restriction by means of the connecting collar 20 is not always necessary.

In the ear-fitting device 4 of the present embodiment, the fitting portion 14 continues to the second restriction wall portion 19*b* via the connecting collar 20. A support projection portion 18*b* projects inward in the radial direction B from the second restriction wall portion 19*b*. Further, the second restriction wall portion 19*b* continues to the support plate portion 18*a*. A first restriction wall portion 19*a* continues to the outer edge of the support plate portion 18*a*. As described above, in the ear-fitting device 4 of the present embodiment, the fitting portion 14 as the contact portion 11 and the retainer portion 13 are connected to each other via the connecting collar 20. In this embodiment, while the fitting portion 14 and the retainer portion 13 are integrally formed via the connecting collar 20, at least one of the retainer portion 13, the fitting portion 14, and the connecting collar 20 may be formed separately and joined together by adhesion, welding, or the like.

As depicted in FIG. 6, the support plate portion 18*a* in the present embodiment faces the lower surface of the base end portion 12*a* of the insert portion 12 described above with a gap in the height direction A therebetween. The hold portion 2*b* of the warming body 2 may be inserted from the inside to the outside in the radial direction B between the lower surface of the base end portion 12*a* of the insert portion 12 and the upper surface of the support plate portion 18*a*. In addition, as depicted in FIG. 6, the first restriction wall portion 19*a* extends upward from the outer edge portion of the support plate portion 18*a* in the radial direction B and continues to the base end portion 12*a* of the insert portion 12.

<Connecting Collar 20>

As described above, the ear-fitting device 4 in the present embodiment includes the connecting collar 20 in addition to the contact portion 11, the insertion portion 12 and the retainer portion 13. The connecting collars 20 in the present embodiment continue to the fitting portion 14 as the contact portion 11. More specifically, the connecting collar 20 in the present embodiment projects outward in the radial direction B from the lower end of the fitting portion 14 and connect the fitting portion 14 and the second restriction wall portion 19*b* of the retainer portion 13 with each other. Further, as depicted in FIGS. 5B and 6, the connecting collar 20 in the present embodiment includes a free end portion 20*a* that does not continue to the second restriction wall portion 19*b* of the retainer portion 13 at the outer edge portion in the radial direction B. As depicted in FIGS. 5B, 6 and 7, the lower surface of the free end portion 20*a* is formed with a ventilation groove 21 that extends to a recess provided at the lower end of the fitting portion 14 and communicates with the accommodation space 15*a*. Thus, even if the hold portion 2*b* of the warming body 2 is in contact with the lower end of the fitting portion 14 and the connecting collar 20 in a state where the body portion 2*a* of the warming body 2 is accommodated in the accommodation space 15*a*, it is possible to introduce air into the accommodation space 15*a* through the ventilation groove 21. Thus, even if the main body portion 2*a* containing the exothermic composition 5 (see FIG. 4) for generating heat by contact with air is accommodated in the accommodation space 15*a*, the air can be introduced into the accommodation space 15*a* through the ventilation grooves 21 to generate heat.

As depicted in FIG. 2, in this embodiment, with the warming body 2 attached to the ear-fitting device 4, part of the hold portion 2*b* of the warming body 2 is exposed further outside in the radial direction B than the outer edge of the free end portion 20*a*. Thus, when removing the warming body 2 from the ear-fitting device 4, the part exposed from the outer edge of the free end portion of the hold portion 2*b* in the warming body 2 can be gripped and operated. By this, the warming body 2 can be easily removed from the ear-fitting device 4.

Further, as depicted in FIG. 5A, the connecting collar 20 in the present embodiment is not provided on both sides of the insert portion 12 in the circumferential direction D of the fitting portion 14 (which, in the present embodiment, is same as the circumferential direction of the annular side wall and may be simply referred hereinafter as "the circumferential direction D"). Thus, the ear-fitting device 4 in the present embodiment is configured so that the upper surface of the support plate portion 18*a* can be visually recognized in a top view as depicted in FIG. 5A. In the warming body 2 of the present embodiment, the hold portion 2*b* may be attached to the ear-fitting device 4 by being inserted between the lower surface of the base end portion 12*a* of the insert portion 12 and the upper surface of the support plate portion 18*a* from the inside to the outside in the radial direction B. Thus, since the connecting collar 20 is not provided on both sides of the insert portion 12 in the circumferential direction D, is it possible to visually recognize from the outside whether or not the hold portion 2*b* of the warming body 2 has been properly inserted between the lower surface of the base end portion 12*a* of the insert portion 12 and the upper surface of the support plate portion 18*a*.

While the ear-fitting device 4 of the present embodiment includes a connecting collar 20 projecting outward in the radial direction B from the lower end of the fitting portion 14 for connecting the fitting portion 14 as the contact portion 11 and the retainer portion 13 with each other, the configuration of the connecting collar 20 of the present embodiment is not limited as long as the fitting portion 14 and the retainer portion 13 are connected to each other. However, as in the present embodiment, it is preferred to provide the connecting collar 20 having a lower surface at the same position in the height direction A as the lower end of the fitting portion 14. By this, with the body portion 2*a* of the warming body 2 accommodated in the accommodation space 15*a*, the flange-shaped hold portion 2*b* of the warming body 2 is suppressed from moving so as to be inclined with respect to the height direction A. As a result, the body portion 2*a* of the warming body 2 is less likely to come off from the accommodation space 15*a*. Thus, it is possible to further enhance the positional stability of the warming body 2 in a state where the hold portion 2*b* of the warming body 2 is retained by the retainer portion 13.

The material forming the ear-fitting device 4 is not particularly limited, and examples thereof may include, for example, rubber, elastomer, synthetic resins including soft resin and hard resin. More specifically, examples may include polypropylene (PP), polyethylene (PE), polyethylene terephthalate (PET), elastomers, and the like. In terms of efficient transmission of the heat of the warming body 2 to the auricle AU (see FIG. 3), the material forming the ear-fitting device 4 may be a material with high thermal conductivity. Examples of such materials may include those in which thermal conductivity is enhanced by mixing a base material such as rubber, elastomer, or synthetic resin, with a material having high thermal conductivity, such as metal or carbon. Also, there may be used a thermally conductive resin having a high thermal conductivity.

<Positional Relationship Between the Warming Body 2 and the Ear-Fitting Device 4 in the Warming Device 100 in Use>

Figure 9:
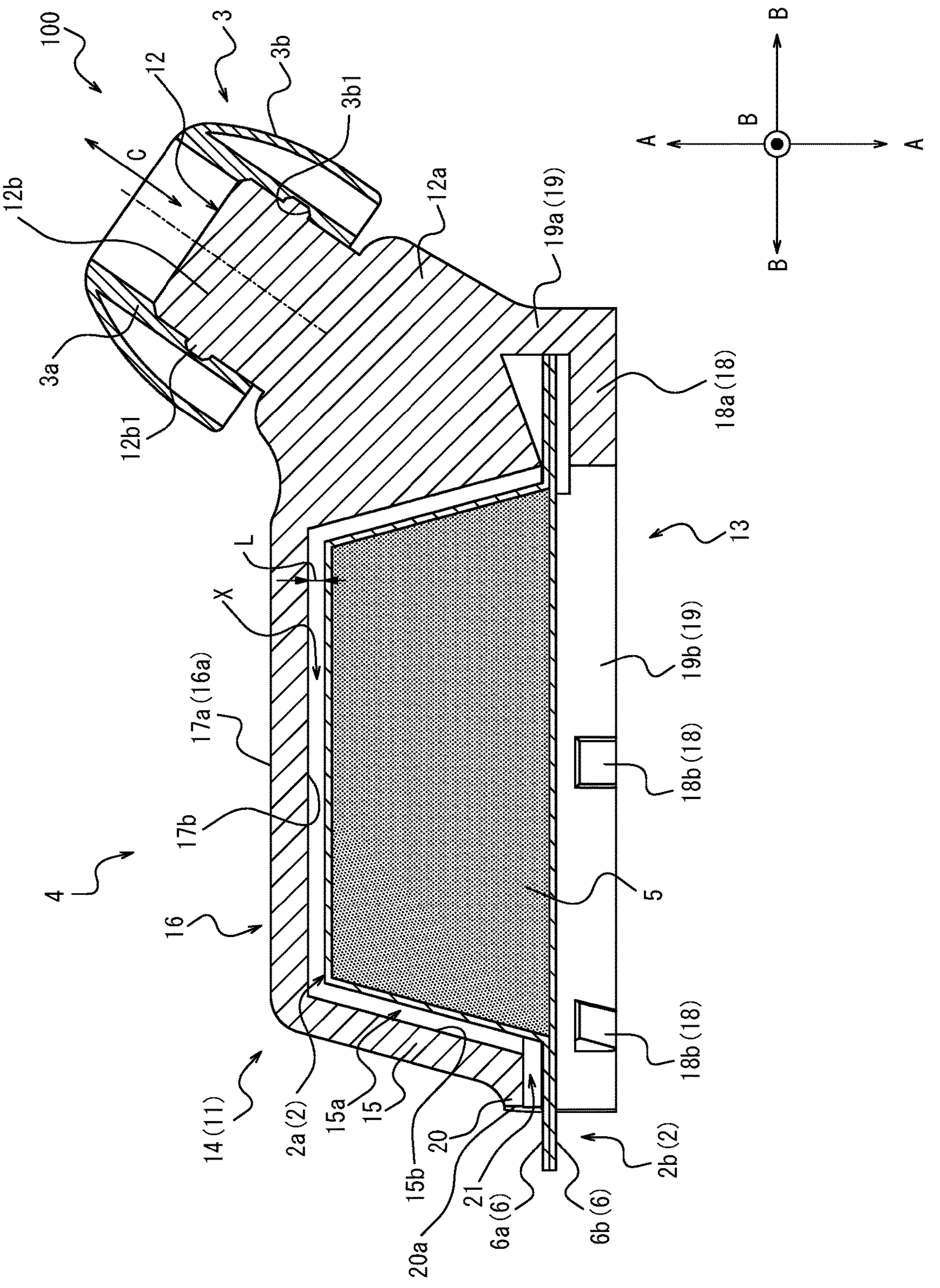
FIG. 9 is a sectional view depicting the warming device of FIG. 2 in use.
Figure 10:
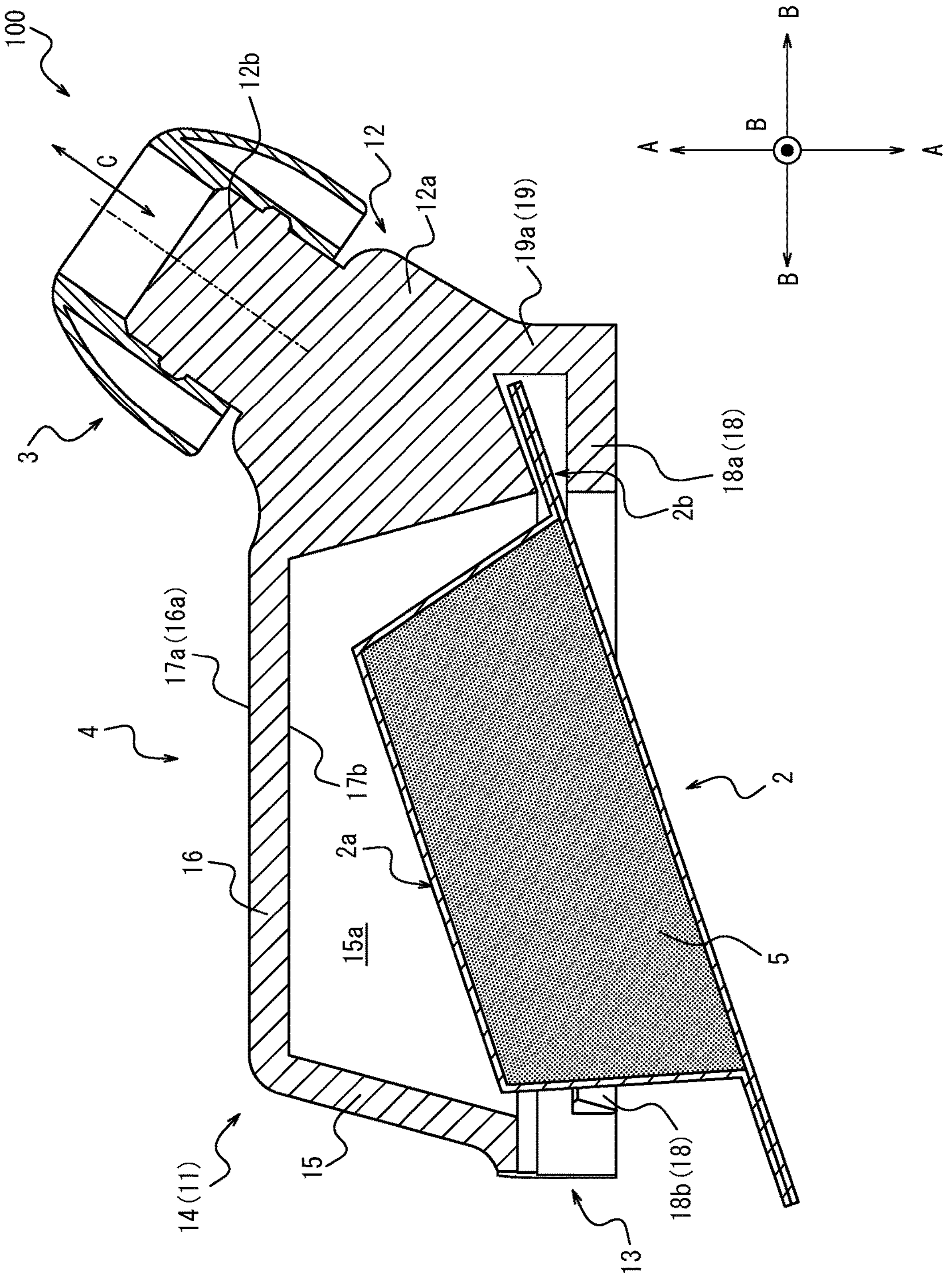
FIG. 10 is a sectional view depicting a state where a warming body is being attached to the ear-fitting device of FIG. 1.

FIG. 9 is a sectional view depicting the warming device 100 in use, in which the warming body 2 and the cover member 3 are attached to the ear-fitting device 4. FIG. 9 depicts a section at the same position along the line I-I in FIG. 5 in a state where the warming body 2 and the cover member 3 has been attached to the ear-fitting device 4. Also, FIG. 10 is a sectional view depicting a state where the warming body 2 is being attached to the ear-fitting device 4, at the same position as FIG. 9. Hereinafter, the positional relationship between the warming body 2 and the ear-fitting device 4 in the warming device 100 in use will be described.

As depicted in FIG. 9, the retainer portion 13 is configured to retain the warming body 2 for warming a predetermined site of the auricle AU (see FIG. 3) through the contact portion 11. In the present embodiment, as described above, in a state where the body portion 2*a* of the warming body 2 is accommodated in the accommodation space 15*a*, the support portion 18 and the restriction wall 19 of the retainer portion 13 are aligned with the hold portion 2*b* of the warming body 2.

The retainer portion 13 serves to restrict the movement of the warming body 2 with respect to the ear-fitting device 4 within a predetermined range so that the warming body 2 is not spaced from the ear-fitting device 4. That is, the configuration of the retainer portion 13 is not limited to one where the warming body 2 is retained immovably with respect to the ear-fitting device 4 at all.

As depicted in FIG. 9, the retainer portion 13 of this embodiment holds the hold portion 2*b* of the warming body 2 so as to be movable in the height direction A within a predetermined range. Specifically, the retainer portion 13 of the present embodiment retains the warming body 2 such that the warming body 2 is movable in the height direction A, within the range from a position where the lower surface of the hold portion 2*b* is in contact with, and supported by the support plate portion 18*a* and the support projection portion 18*b*, up to a position where the upper surface of the hold portion 2*b* is brought into contact with the lower end of the fitting portion 14 and the lower surface of the connecting collar 20. FIG. 9 depicts the uppermost retaining position of the warming body 2 where the upper surface of the hold portion 2*b* of the warming body 2 is in contact with the lower end of the fitting portion 14 and the lower surface of the connecting collar 20.

Furthermore, as depicted in FIG. 9, the retainer portion 13 in the present embodiment serves to retain the hold portion 2*b* of the warming body 2 in a state where it cannot move in the direction perpendicular to the height direction A. Specifically, in this embodiment, the first restriction wall portion 19*a* and the second restriction wall portion 19*b* of the restriction wall 19 are located around the hold portion 2*b* of the warming body 2 in the direction perpendicular to the height direction A. Thus, the first restriction wall portion 19*a* and the second restriction wall portion 19*b* of the restriction wall 19 are in contact with the outer edge of the hold portion 2*b* of the warming body 2, thereby restricting the warming body 2 from movement in the direction perpendicular to the height direction A. However, as described above, the retainer portion 13 may be configured to retain the hold portion 2*b* of the warming body 2 so as to be movable in the direction perpendicular to the height direction A within a predetermined range.

Here, as depicted in FIG. 9, the retainer portion 13 serves to retain the warming body 2 while being spaced from the contact portion 11 with a gap X therebetween. More specifically, the retainer portion 13 in the present embodiment serves to retain the warming body 2 while being spaced from the fitting portion 14 as the contact portion 11, with the gap X therebetween. Note that when the retainer portion 13 retains the warming body 2 movably within a predetermined range as in the present embodiment, the warming body 2 at any position within the predetermined movable range is in a state of being spaced from the fitting portion 14 as the contact portion 11 with the gap X therebetween. For example, while FIG. 9 depicts a state in which the warming body 2 is in the uppermost retaining position, even in such a state the main body portion 2*a* of the warming body 2 is maintained in a state spaced from the annular side wall 15 and the top plate portion 16 of the fitting portion 14 with the gap X therebetween.

In this way, by using the retainer portion 13 to retain the warming body 2 for warming a predetermined site of the auricle AU (see FIG. 3) through the contact portion 11, with the warming body 2 being spaced from the contact portion 11 with a gap X therebetween, it is possible to suppress an abrupt temperature rise of the contact portion 11, and suppress occurrence of burns in the predetermined site of the auricle AU with which the contact portion 11 contacts.

Further, in the retainer portion 13 of the present embodiment, the warming body 2 is retained in a state where the warming body 2 is accommodated inside the annular side wall 15 from the side of the top plate lower surface 17*b* that is the back side of the top plate upper surface 17*a* as the contact surface 16*a* of the top plate portion 16. By configuring the retainer portion 13 to retain the warming body 2 that is accommodated in the accommodation space 15*a* in the annular side wall 15 as described above, the warming body 2 can be easily attached to the ear-fitting device 4.

More specifically, as depicted in FIG. 9, the retainer portion 13 in the present embodiment retains the hold portion 2*b* projecting from the body portion 2*a* of the warming body 2 in a state where the main body portion 2*a* of the warming body 2 is accommodated inside the annular side wall 15 from the side of the top plate lower surface 17*b* of the top plate portion 16. By this, the warming body 2 can be easily attached to the ear-fitting device 4 as described above. Furthermore, since the hold portion 2*b* of the warming body 2 is brought into contact with the lower end of the annular side wall 15, the pushing amount of the body portion 2*a* into the annular side wall 15 can be restricted. Thus, as depicted in FIG. 9, in a state where the retainer portion 13 retains the hold portion 2*b* of the warming body 2 and the hold portion 2*b* of the warming body 2 is in contact with the lower end of the annular side wall 15, it is readily possible to realize a configuration where the body portion 2*a* of the warming body 2 is spaced from the top plate portion 16 with the gap X therebetween. Therefore, it is possible to suppress occurrence of burns due to the contact surface 16*a* in contact with the bottom surface of the ear concha CA.

Furthermore, as depicted in FIG. 9, in a state where the retainer portion 13 retains the hold portion 2*b* of the warming body 2 and the hold portion 2*b* of the warming body 2 is in contact with the lower end of the annular side wall 15, the body portion 2*a* of the warming body 2 in the present embodiment is spaced not only from the top plate portion 16 but also from the annular side wall 15 with the gap X therebetween. By this, it is also possible to suppress occurrence of burns due to the outer surface of the annular side wall 15 in contact with the inner surface of the ear concha CA.

As depicted in FIG. 10, in the warming device 100 of the present embodiment, the body portion 2*a* of the warming body 2 is accommodated in the accommodation space 15*a* inside the annular side wall 15 from the lower end side of the annular side wall 15, by inserting the flange portion as the hold portion 2*b* of the warming body 2 into the gap between the support plate portion 18*a* and the insert portion 12 from the inner side in the radial direction B to the outside. The accommodation of the main body portion 2*a* in the annular side wall 15 is completed when, among the hold portion 2*b* of the warming body 2, the portion other than the portion to be inserted into the gap between the support plate portion 18*a* and the insert portion 12 overrides the support projection portion 18*b*, that is, when the hold portion 2*b* is retained by the retainer portion 13.

Further, as depicted in FIG. 9, the retainer portion 13 in the present embodiment serves to retain the warming body 2 in a state where the warming body 2 is covered with the contact portion 11. Specifically, the retainer portion 13 in the present embodiment retains the warming body 2 in a state where the fitting portion 14 as the contact portion 11 covers the body portion 2*a* of the warming body 2. As described above, the provision of the gap X between the contact portion 11 and the warming body 2 serves to suppress an abrupt temperature rise of the contact portion 11, though there may be a possibility that the warming efficiency of warming may be significantly lowered. Thus, in the present embodiment, the warming body 2 is covered with the contact portion 11 across the gap X, so that the atmosphere temperature of the gap X is less likely to be lowered even though the gap X is provided. In other words, by covering the warming body 2 with the contact portion 11, the air gap X can be easily kept warm as compared with a configuration where the warming body 2 is uncovered. This makes it possible to suppress the deterioration in the warming efficiency of the contact portion 11 due to the warming body 2.

It is preferred that the contact portion 11 covers at least the surface of the warming portion of the warming body 2 for warming the contact portion 11. Thus, like the fitting portion 14 as the contact portion 11 in the present embodiment, there may be adopted a configuration where the surface of the body portion 2*a* as the warming portion for warming the fitting portion 14 of the warming body 2 is covered, and the hold portion 2*b*, which is not the warming portion, is uncovered.

Moreover, it is preferred that the distance L between the contact portion 11 and the warming body 2 across the gap X is greater than 0 mm and equal to or less than 1 mm. Here, “the distance L between the contact portion 11 and the warming body 2 across the gap X” means the shortest di stance between the contact portion 11 and any location on the surface of the warming portion of the warming body 2. That is, in the present embodiment, this means the shortest separation distance from any position on the surface of the body portion 2*a* as the warming portion of the warming body 2 to the inner surface 15*b* of the annular side wall 15 or the top plate lower surface 17*b* of the top plate portion 16.

Figure 11:
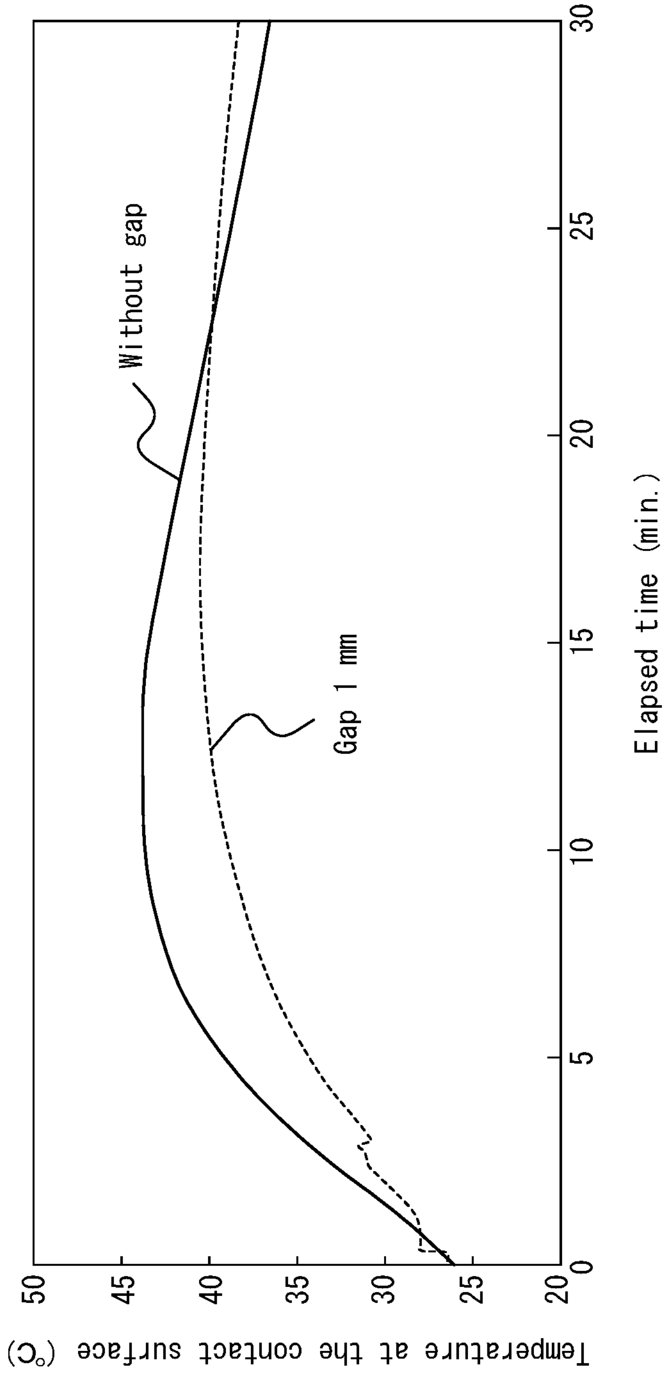
FIG. 11 is a graph depicting the results of an experiment for verifying the effect of the gap depicted in FIG. 9.

FIG. 11 is a graph depicting experimental results of an experiment using the ear-fitting device 4 of the present embodiment, for verifying the effect of the gap X. In this experiment, the temperature of the contact surface 16*a* has been measured with respect to a case where the body portion 2*a* of the warming body 2 is in contact with the top plate lower surface 17*b* of the top plate portion 16 of the ear-fitting device 4 (when there is no gap X), and a case where the body portion 2*a* of the warming body 2 is spaced from the top plate lower surface 17*b* of the top plate portion 16 of the ear-fitting device 4 by 1 mm (when there was a gap X with a separation distance L of 1 mm). In the graph depicted in FIG. 11, the horizontal axis is the elapsed time, and the vertical axis is the temperature of the contact surface 16*a*.

It can be appreciated from FIG. 11 that the provision of the gap X makes it possible to suppress an abrupt temperature rise of the contact surface 16*a*. It can also be appreciated from FIG. 11 that, if the separation distance L is 1 mm, an abrupt lowering in warming efficiency due to heat radiation from the top plate portion 16 to the gap X can be suppressed and the temperature of the contact surface 16*a* can be sufficiently increased. Therefore, if the separation distance L is set to be larger than 0 mm and equal to or smaller than 1 mm, it is possible to suppress a rapid temperature rise of the contact surface 16*a* and lowering in warming efficiency due to the gap X.

From the above results, it is preferred that the retainer portion 13 holds the warming body 2 so that the distance L from the contact portion 11 to the warming body 2 is greater than 0 mm and equal to or less than 1 mm.

The ear-fitting device and the warming device according to the disclosure are not limited to the specific configurations depicted in the above-described embodiments, and various modifications and changes may be made without departing from the scope of the claims.

REFERENCE SIGNS LIST

2: Warming body
2*a*: Body portion
2*b*: Hold portion
3: Cover member
3*a*: Mounting tube portion
3*a*1: Annular concave portion
3*b*: Outer tube portion
4: Ear-fitting device
5: Exothermic composition
6: Container
6*a*: First sheet
6*b*: Second seat
11: Contact portion
12: Insert portion
12*a*: Base end portion
12*b*: Tip end portion
12*b*1: Annular convex portion
13: Retainer portion
14: Fitting portion
15: Annular side wall
15*a*: Accommodation space
15*b*: Inner surface of the annular side wall
16: Top plate portion
16*a*: Contact surface
17*a*: Top plate upper surface
17*b*: Top plate lower surface
18: Support portion
18*a*: Support plate portion
18*b*: Support projection portion

19: Restriction wall
19*a*: First restriction wall portion
19*b*: Second restriction wall portion
20: Connecting collar
20*a*: Free end portion
21: Ventilation groove
100: Warming device
L: Separation distance
X: Gap
AU: Auricle
CA: Ear concha
EA: External auditory canal
A: Height direction of the fitting portion
B: Radial direction of the annular side wall of the fitting portion
C: Center axis direction of the insert portion
D: Circumferential direction of the fitting portion

The invention claimed is:

1. An ear-fitting device configured to be worn on an ear, comprising:

a contact portion for contacting a predetermined site of an auricle; and a retainer portion configured to retain a warming body for warming the predetermined site of an auricle through the contact portion;

wherein the retainer portion is configured to retain the warming body in a state where it is spaced from the contact portion by an air gap, the contact portion comprises an annular side wall having a first end and a second end, and a top plate portion that continues to the first end of the annular side wall, the retainer portion is configured to retain a hold portion of the warming body, the warming body further having a body portion from which the hold portion projects, the body portion of the warming body is accommodated inside the annular side wall, and the retainer portion is configured to retain the warming body such that the body portion is spaced from the top plate portion by the air gap when the hold portion of the warming body is in contact with the second end of the annular side wall.

2. The ear-fitting device according to claim 1, wherein the retainer portion is configured to retain the warming body in a state where the body portion is spaced from the annular side wall with an air gap therebetween.

3. The ear-fitting device according to claim 1, wherein the retainer portion is configured to retain the warming body such that a distance from the top plate portion to the warming body across the air gap is greater than 0 mm and equal to or less than 1 mm.

4. A warming device comprising the ear-fitting device according to claim 1 and the warming body.

* * * * *